United States Patent [19]

Joung

[11] 4,310,928
[45] Jan. 19, 1982

[54] SURGEON'S GLOVE AND TALC FREE PROCESS FOR FORMING SAME

[75] Inventor: John J. Joung, South Pasadena, Calif.

[73] Assignee: American Hospital Supply Corporation, Evanston, Ill.

[21] Appl. No.: 61,790

[22] Filed: Jul. 30, 1979

[51] Int. Cl.³ .................................................. A41D 19/04
[52] U.S. Cl. ........................................... 2/161 R; 2/168
[58] Field of Search .............. 2/161 R, 168, 169, 167, 2/161 A; 428/447; 36/7.3, 87, 98; 12/142 EV

[56] References Cited

U.S. PATENT DOCUMENTS 2,789,933  4/1957  Bargmeyer ................ 12/142 EV X
3,411,982  11/1968  Kavalir et al. ..................... 2/168 X
4,143,423  3/1979  Sternlieb ................................ 2/168

Primary Examiner—H. Hampton Hunter
Attorney, Agent, or Firm—Mary J. Kanady; Roger A. Williams

[57] ABSTRACT

A surgeon's glove which is free of mold release powder of mineral origin. The glove is "talc free" and contains on a surface a lipo compound and a surfactant for such lipo compound. The glove is manufactured by a process which includes coating a glove form with a coagulant containing the lipo compound and its surfactant in a dispersion which stay with the glove after it is stripped from the mold providing a mold release surface for such glove.

10 Claims, 3 Drawing Figures

SURGEON'S GLOVE AND TALC FREE PROCESS FOR FORMING SAME

BACKGROUND

Surgeon's gloves are made by dipping a hand shaped mold into a coagulant and subsequently into a latex bath. One of the problems with such gloves is that they tend to stick to the mold after the glove is cured. To solve this problem, all commercially made gloves in the United States include in the coagulant dip a powder of mineral origin. The powder is usually talc because talc can withstand the curing temperatures of 260° F.

Because such talc is used in the manufacturing process of latex surgeon's gloves, they must be thoroughly washed after their manufacture to remove all of the excess talc that may be on the surface. Such talc particles were necessary to remove the glove from its dipping form. The medical literature has reported that talc particles might create granuloma when they become in contact with a surgical wound. Talc, being of mineral origin, is not bioabsorbable.

Because of talc particles used in the coagulant solution of all surgeon's gloves are infused or embedded into the glove wall itself during the manufacturing process, some talc particles that are only partially exposed at the surface of the glove are difficult to remove. Efforts to eliminate the talc from the coagulant solution have not been successful. Without the talc in the coagulant, the very thin walled surgeon's gloves tended to rip and ball up into a gummy structure when stripped from the mold.

SUMMARY OF THE INVENTION

The present invention overcomes the problems with surgeon's gloves explained above. This invention provides a surgeon's glove that is free of powder of mineral origin and yet is readily strippable from its mold without tearing, gumming up, etc. The surgeon's glove has on its surface a lipo compound and a surfactant for such compound which withstands the curing temperature of 260° F, as well as providing easy mold release. Lipo compound and the surfactant are in the coagulant and stay with the glove when it is removed from its form.

THE DRAWINGS

DETAILED DESCRIPTION

Figure 1:
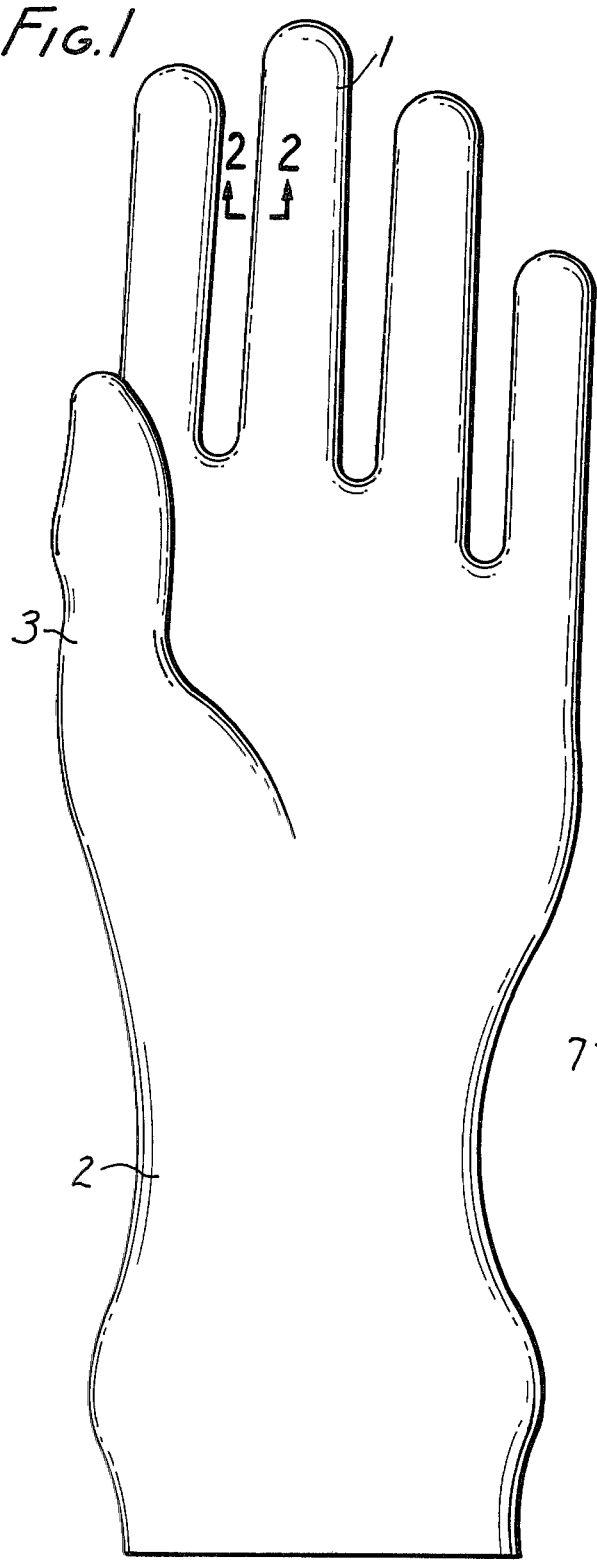
FIG. 1 is a front elevational view of the surgeon's glove.
Figure 2:
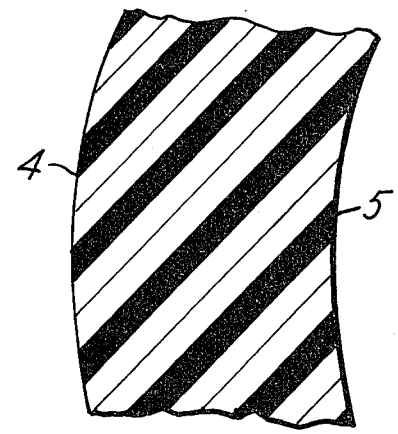
FIG. 2 is an enlarged sectional view taken along line 2—2 of FIG. 1 showing the inner and outer surfaces of the glove.

FIG. 1 shows a surgeon's glove that has a conventional finger area 1, wrist area 2, and thumb area 3. The glove shown here has been stripped from its form and is positioned ready for donning. As shown in FIG. 2, the glove which is highly stretchable is formed of a shell with an outer surface 4 and an inner surface 5. It is inner surface 5 that fits against the surgeon's hands.

Figure 3:
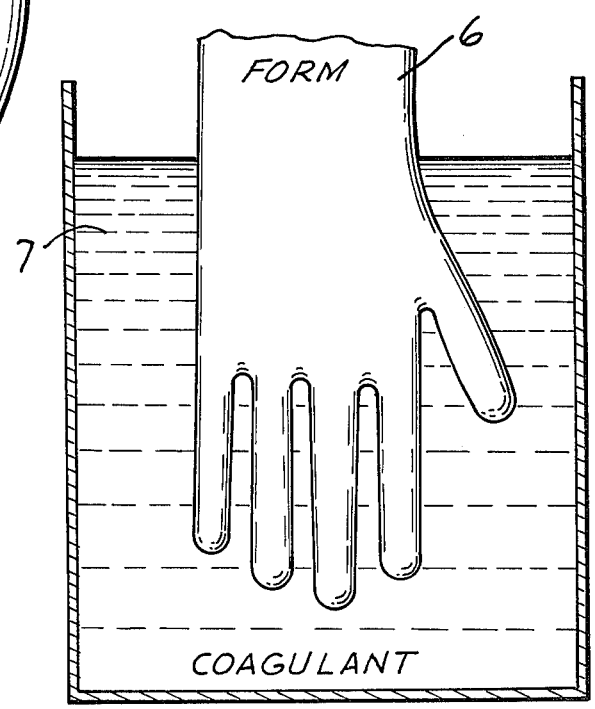
FIG. 3 is a schematic view showing the glove form being dipped into a coagulant.

Usually such surgeon's gloves are formed by dip coating a hand shaped form, such as 6 in FIG. 3, into a coagulant 7. From removal of the coagulant coated form from a coagulant tank, it is then dipped into a latex dispersion to coat the form and combine with the coagulant to form a gel on the form of the proper thickness to produce the glove.

So that the glove could be stripped from its form, the conventional surgeon's gloves are made with talc powders suspended in the coagulant. However, in the present invention, all talc is eliminated from the coagulant solution. Instead, a lipo compound is included in the coagulant.

The lipo compound can include lipids or lipophilic substances, such as fatty acids, fatty acid esters, fatty acid salts, cholesterols, polyols, paraffin oils, mineral oils, vegetable oils, silicones, alkyl polyether alcohols and aryl polyether alcohols. Other lipophilic polymers could also be used as long as they are biologically compatible with the human body.

A problem with a lipo compound in the coagulant occurs because it separates from the coagulant, particularly when dipped into a water based latex bath. Since it separates, a lipo compound cannot function properly as a mold release. A surfactant combined with the lipo compound overcomes this problem.

The term "surfactant" is used in a broad meaning to include various surfactants, detergents, and dispersing agents, as well as amphoteric surface active agents. Typical surfactants for use in the present invention include polysorbate, polyoxyethylene sorbitan, polyethyleneoxy derivatives, fatty acid salts, alkyl-aryl sulfonates, alkyl sulfonates, alkyl sulfates, and silicone glycols.

In preparing the coagulant solution, an aliquot of lipo compound is mixed with an exact amount of surfactant in aqueous solution, and then mixed with the remaining components of the coagulant. Sometimes heating is necessary to disperse the lipo compounds. The amount of surfactant should be enough to disperse the lipid into colloid or translucent dissolution. Excessive amounts of surfactant will result in excessive loss of the lipo compound during extraction, as well as cause foaming. Too small an amount of surfactant will cause lipid droplets to float on the coagulant surfaces resulting in pin holes in gloves or other latex products. Depending upon the application, as well as the particular chemicals, the lipo compound and the surfactant each are present in the coagulant in a range of 0.2 to 3% by weight. Preferably, the lipo compound and surfactant are present such that a stable dispersion can be achieved in the coagulant solution without excessive foaming.

Although the mechanism of the lipo compound and the surfactant is not totally understood, it is believed to cause mold release of the rubber product as follows:

(1) The dispersed lipid and other nonvolatile components form a uniform film when the form is dipped and dried.

(2) When the form is dipped into the latex, the film release coagulant forms latex coagulum, trapping the lipid dispersion between the form and coagulum.

(3) Upon extraction, the surfactant, being water soluble, can more readily diffuse out with other components of coagulant through the latex coagulum layer, whereas the lipo compound is more difficult to pass through the organophilic coagulum. Therefore, tiny lipo compound dispersion surrounded by surfactant molecules are created between the form and coagulum. The lipo compound phase facilitates form release and everything attaches to the form surface of the glove or rubber product resulting in tack free surfaces, and the form (which can be a ceramic glove form) becomes free of the lipo compound. Repeated dipping tests indicate the lipo compound need not be detergently cleansed from the form before the next glove is made.

It is very important to understand that any mold release agent in the coagulant must also withstand the curing heat of approximately 260° F. and also have minimal plasticizing effect on the cured rubber. The improved coagulant with the lipo compound and surfactant of the present invention meets this criteria.

EXAMPLE 1

A coagulant was prepared according to the following formulation. The coagulant contains 0.5% alkylaryl polyether alcohol (Triton X 100; Rohm & Haas Co., 5000 Richmond, Philadelphia, Penn.) dispersed by a polyethyleneoxy derivative (Emulphor ON-877; GAF, 189 Wells Avenue, Newton, Mass.).

| Coagulant Formulation | |
|---|---|
| Composition | Weight % |
| Ca (NO$_3$)$_2$ | 15 |
| Zn (NO$_3$)$_2$ | 10 |
| Triton × 100 | 0.5 |
| Emulphor ON-877 | 0.7 |
| Water | 18.8 |
| Ethanol | 65 |

The gloves were prepared using 30% solid content natural rubber latex and cured at 260° F. for 30 minutes after extracting the coagulum for 5 minutes in running tap water. The gloves came off from the forms easily and the surface of the glove was not tacky.

EXAMPLE 2

Polydimethylsiloxane (viscosity 100,000 C.P.) was dispersed into the coagulant as shown in the following table. When the coagulant was used to make a glove, excellent form release characteristics, as well as a slippery surface on the glove, resulted.

| Coagulant Formulation | |
|---|---|
| Composition | Weight % |
| Ca (NO$_3$)$_2$ | 20 |
| Silicone Fluid | 0.3 |
| Emulphor ON-877 | 1.2 |
| Ethyl Alcohol | 25 |
| Water | 53.5 |

EXAMPLE 3

Sorbitan Monooleate was incorporated into the coagulant by using a dispersing agent, polyoxyethylene sorbitan monooleate (Tween 80; ICI, Wilmington, Delaware). The resultant rubber glove surface felt like a leather surface. The formulation is shown in the following table.

| Coagulant Formulation | |
|---|---|
| Composition | Weight % |
| Ca (NO$_3$)$_2$ | 10 |
| Zn (NO$_3$)$_2$ | 10 |
| Sorbitan monooleate | 1 |
| Tween 80 | 1 |
| Ethanol | 60 |
| Ethyl lactate | 0.5 |
| Water | 17.5 |

EXAMPLE 4

Equal amounts of sorbitan stearate and Tween 80 were mixed together. In the mixture, water was added (4 fold by weight) and heated. The stearate dispersed vigorously upon heating by a burner and formed a colloidal suspension. In this case, the coagulant formulation was:

| Composition | Weight % |
|---|---|
| Lipid suspension | 3.5 |
| Ca (NO$_3$)$_2$ | 16 |
| Zn (NO$_3$)$_2$ | 10 |
| Water | 20 |
| Alcohol | 60 |
| Ethyl lactate | 0.5 |

EXAMPLE 5

One Kg of mineral oil was added into 4 Kg of Emulphor ON-877 and homogenized by vigorous mixing. A mineral oil containing coagulant was prepared with it. In this case, the coagulant formulation was:

| Composition | Weight % |
|---|---|
| Ca (NO$_3$)$_2$ | 15 |
| Zn (NO$_3$)$_2$ | 5 |
| Water | 15 |
| Mineral oil suspension | 2.5 |
| Ethyl lactate | 0.5 |
| Ethyl alcohol | 62 |

In a related application entitled "Lipo-Surfactant Coagulant For Rubber," filed July 30, 1979, Ser. No. 061,789, the coagulant per se is described and claimed. In the present application, the surgeon's glove made by the process that uses such coagulant is described and claimed. Here the surgeon's glove is made by a process of coating the glove form with a coagulant having a lipo compound and a surfactant, applying a latex layer to the coated form, extracting the undesired portions of the coagulant, such as solvents, etc. leaving the lipo compound and its surfactant on the glove, curing the glove and then stripping it from the mold.

It is important to note that the lipo compound and its surfactant goes with the glove when it is removed from its form, thus cleaning the glove form for a subsequent dip forming of an additional glove. The lipo compound and its surfactant are biologically compatible with the human body and in most instances, will be bioabsorbable. A powder of mineral origin, such as talc, is not bioabsorbable because it will not dissolve in body fluids.

The resultant glove containing the lipo compound and surfactant can also be used as the support glove for subsequently covalently bonding to a silicone barrier glove as described in a related application entitled "Hypoallergenic Slip Resistant Gloves and Methods of Making Same," filed July 30, 1979, Ser. No. 061,788. Such glove can also be halogenated after forming to provide a surgeon's glove that does not need any lubricating donning powder, such as starch. Its halogenated glove is described in a copending application entitled "Donable Surgeon's Glove Free of Inner Surface Lubricating Powder and Method of Making Same," Filed July 30, 1979, Ser. No. 061,787.

In the foregoing description, specific examples have been used to describe the invention. However, it is understood by those skilled in the art that certain modifications can be made to these examples without departing from the spirit and scope of the invention.

I claim:

1. A surgeon's glove comprising a highly stretchable latex shell that is free of powder of mineral origin, wherein the glove has a lipo compound carried on its surface and a surfactant for the lipo compound on its surface, whereby the glove is strippable from a form.

2. A surgeon's glove as set forth in claim 1, wherein the lipo compound and surfactant are embedded within the latex shell as well as on its surface.

3. A surgeon's glove as set forth in claim 1, wherein the lipo compound and surfactant are approximately equivalent.

4. A surgeon's glove as set forth in claim 1, wherein the lipo compound is selected from the group consisting of lipids and lipophilic polymers; and the surfactant is nonionic.

5. A surgeon's glove as set forth in claim 1, wherein the lipo compounds are selected from the group consisting of fatty acids, fatty acid esters, fatty acid salts, cholesterols, polyols, paraffin oils, mineral oils, vegetable oils, silicones, alkyl polyether alcohols, and aryl polyether alcohols.

6. A surgeon's glove as set forth in claim 1, wherein the surfactant is nonionic and is selected from the group consisting of polysorbate, polyoxyethylene sorbitan, polyethyleneoxy derivatives, fatty acid salts, alkyl-aryl sulfonates, alkyl sulfates, and silicone glycols.

7. A surgeon's glove as set forth in claim 1, wherein the surfactant is selected from the group consisting of nonionic, ionic, and amphoteric surface acting agents.

8. A surgeon's glove as set forth in claim 1, wherein the glove is talc free.

9. A surgeon's glove which has a lipo compound carried on its surface and a surfactant for the lipo compound on its surface, whereby the glove is strippable from a form.

10. A surgeon's glove as set forth in claim 9, wherein the lipo compound is a mineral oil.

* * * * *